US010346587B2

(12) United States Patent
Stamper et al.

(10) Patent No.: US 10,346,587 B2
(45) Date of Patent: Jul. 9, 2019

(54) PATIENT/MEMBER RECONCILED BILLING AND EXPLANATION OF BENEFIT STATEMENTS WITH PROVIDER PROMPT PAY

(75) Inventors: Jeanne Stamper, Lexington, KY (US); Paul Alan Hartley, New Canaan, CT (US); Mike Morrison, Lexington, KY (US)

(73) Assignee: Conduent Business Services, LLC, Dallas, TX (US)

( * ) Notice: Subject to any disclaimer, the term of this patent is extended or adjusted under 35 U.S.C. 154(b) by 209 days.

(21) Appl. No.: 13/562,977

(22) Filed: Jul. 31, 2012

(65) Prior Publication Data

US 2014/0039905 A1    Feb. 6, 2014

(51) Int. Cl.
| G06F 19/00 | (2018.01) |
| G06Q 30/04 | (2012.01) |
| G06Q 20/14 | (2012.01) |
| G06Q 50/22 | (2018.01) |
| G06Q 20/10 | (2012.01) |

(52) U.S. Cl.
CPC ........... *G06F 19/328* (2013.01); *G06Q 30/04* (2013.01); *G06Q 20/102* (2013.01); *G06Q 20/14* (2013.01); *G06Q 50/22* (2013.01)

(58) Field of Classification Search
CPC .............................................. G06Q 50/22–24
USPC ....................................................... 705/2, 3
See application file for complete search history.

(56) References Cited

U.S. PATENT DOCUMENTS

| 7,996,239 | B1* | 8/2011 | Pellican et al. .................... 705/2 |
| 2004/0243441 | A1* | 12/2004 | Bocionek et al. ................. 705/2 |
| 2005/0033609 | A1* | 2/2005 | Yang ................................. 705/2 |
| 2008/0052127 | A1* | 2/2008 | Rosenfeld et al. ............... 705/3 |
| 2008/0120136 | A1* | 5/2008 | Barrett .............................. 705/2 |
| 2010/0017231 | A1* | 1/2010 | Galbraith et al. ................ 705/3 |
| 2011/0178816 | A1* | 7/2011 | Lee et al. .......................... 705/2 |
| 2011/0258004 | A1* | 10/2011 | Dean et al. ....................... 705/4 |
| 2011/0270749 | A1* | 11/2011 | Bennett et al. ................ 705/40 |
| 2011/0313784 | A1* | 12/2011 | Harvey et al. .................... 705/2 |
| 2012/0078646 | A1* | 3/2012 | Toleti et al. ...................... 705/2 |
| 2012/0253868 | A1* | 10/2012 | Ach et al. .................... 705/7.12 |
| 2013/0117035 | A1* | 5/2013 | Tierney et al. ................... 705/2 |
| 2013/0117045 | A1* | 5/2013 | Kusens ............................. 705/3 |

OTHER PUBLICATIONS

"How Simplee Works," http://simplee.com/how-simple-works, downloaded from the Internet Apr. 16, 2012, 4 pages.
"Pompt Pay Inc. Eliminates Billing," http://www.promptpay.com/works.html, downloaded from the Internet Apr. 16, 2012, 1 page.

* cited by examiner

*Primary Examiner* — Jonathan Ng
(74) *Attorney, Agent, or Firm* — Conley Rose, P.C.

(57) ABSTRACT

A healthcare payment management system comprising a payment consolidation server configured to receive billing information from a provider for an episode of care for a member, receive benefit information from a payer for the episode of care, consolidate the billing information and the benefit information into a payment reconciliation statement, and send the payment reconciliation statement to a member.

16 Claims, 4 Drawing Sheets

PATIENT/MEMBER RECONCILED BILLING AND EXPLANATION OF BENEFIT STATEMENTS WITH PROVIDER PROMPT PAY

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Health plan members or patients often receive multiple communications from healthcare payers (e.g., health insurance companies) and providers (e.g., doctors, hospitals, care centers/clinics). The communications may include bills, invoices, and statements regarding episodes of care to providers (e.g., clinical visits, treatments). For example, the same care visit or treatment for a patient may result in multiple explanations of benefits (EOBs) according to payer(s) and multiple billing statements for different providers (e.g., physicians, nurse practitioners, labs). Reconciling the billing statements against the EOBs and the various EOB components (deductibles, coverage percentage) to determine what is really owed by the member/patient can be often challenging. Further, this reconciliation is typically done in the context of health spending accounts (HSAs), flexible spending accounts (FSAs), high deductible plans, provider network discounts, and/or other guidelines, where indicated figures and values are not easily mapped or understood. As a result, patients may delay or choose not to pay providers, which causes significant underpayment of providers. The underpaid providers may also choose not to pursue payment due to the relatively high administrative cost associated with reconciliation and collections. The underpayment of providers is one aspect that contributes to overall healthcare cost.

SUMMARY

In an embodiment, the disclosure includes a healthcare payment management system comprising a payment consolidation server configured to receive billing information from a provider for an episode of care for a member, receive benefit information from a payer for the episode of care, consolidate the billing information and the benefit information into a payment reconciliation statement, and send the payment reconciliation statement to a member.

In another embodiment, the disclosure includes an apparatus comprising an apparatus for healthcare payment management comprising a processor configured to receive one or more billing statements from one or more providers for an episode of care for a member, receive one or more EOB statements from one or more payers for the episode of care, and consolidate the billing statements and the EOB statements to provide a total balance owed by the member to each of the providers for the episode of care, wherein the total balance includes any payments the payer will make or has made on behalf of the member for the episode of care.

In yet another embodiment, the disclosure includes a healthcare payment management method comprising receiving billing information from one or more providers for one or more healthcare services to a member, receiving healthcare insurance benefits information from one or more payers for the one or more healthcare services, generating a payment reconciliation statement for the member by consolidating and mapping between the billing information and the healthcare insurance benefits information, sending the payment reconciliation statement and the one or more payment options to the member, and presenting one or more payment options to the member including a multiple payments option.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
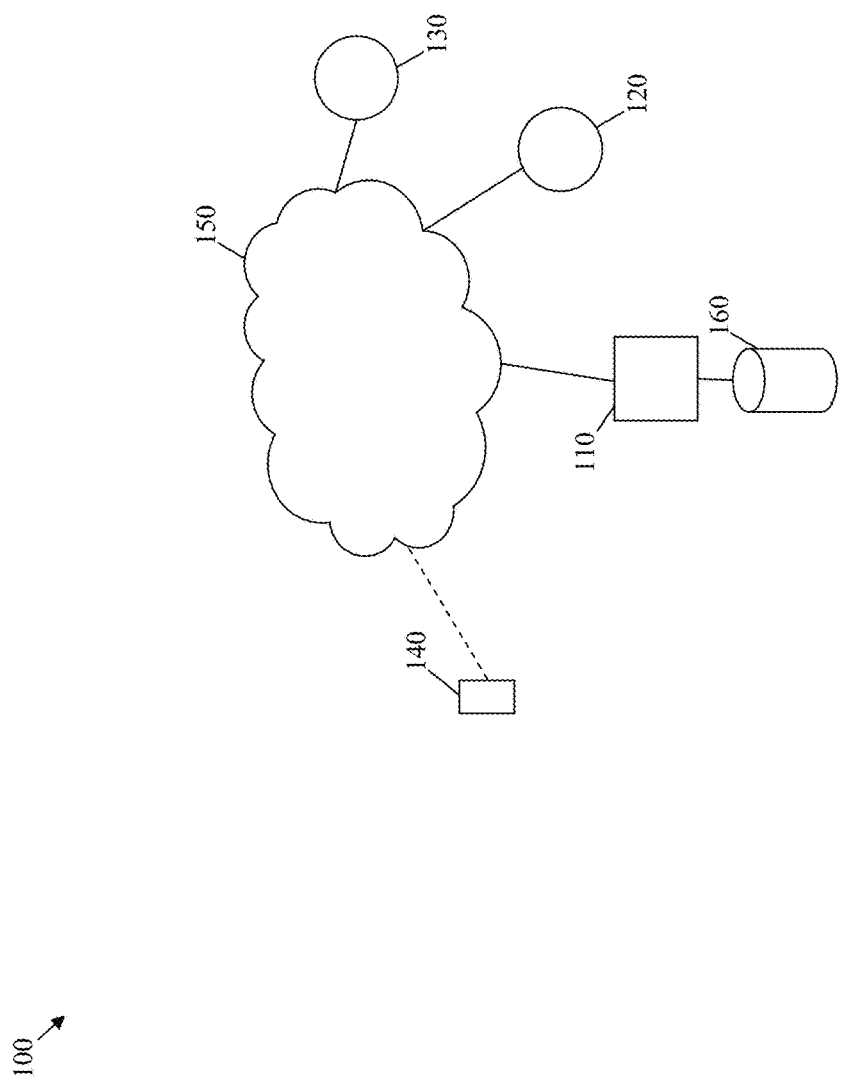
FIG. 1 is a schematic diagram of an embodiment of a healthcare payment management system.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The size of bills for healthcare services by providers is estimated to be in hundreds of billions of dollars, where about half of all bills owed by patients are not paid promptly or go unpaid. For example, for every about ten billion dollars of healthcare service provided, the payers (e.g., insurance companies) may pay about 80 percent or about eight billion dollars. Of the remaining about two billion dollars, approximately one billion dollars may be paid and the remaining may be collected at relatively high cost or may never be collected. Thus, improving the amount of these past-due collections by at least about ten percent may increase the value to providers by about a hundred million dollars, which may be an overall improvement in collections about one percent. If the overall healthcare market is estimated to be in the order of five hundred billion dollars annually, then the value to providers may be about five billion dollars per year.

Currently, reconciling bills issued by providers to health plan members/patients may be a process substantially handled by members/patients. Since balance due may not be determined at point of care (e.g., patient visit to provider), providers may use billing companies to manage collections post care. Payments are typically made by sending paper checks or credit card authorizations to the providers and/or the collection agencies. In the case of non-payment of bills by members/patients, the providers may resort to collection programs or write off the unpaid bills. Some members/patients may choose not to pay providers due to difficulties to understand and/or reconcile billing statements from providers against EOB information from payers, which may cause substantial underpayments of providers. Resolving the issue of underpayments of providers by members/patients may depend on improving the handling of EOBs and billing statements information and facilitating the reporting of such information to members/patients.

Disclosed herein is a system and method for promoting payments from members/patients to providers and improving the payment process. The system and method may eliminate or substantially reduce underpayment by members/patients to providers by facilitating the understanding and reconciling of bills and the handling of payments for the members/patients. The system and method may consolidate EOBs and billing statements information for members/patients and report the consolidated information to members/patients to facilitate payment decisions. The system and method may also facilitate the payment process for members/patients by providing convenient payment options (e.g., electronic payments), such as using the members/patients' HSAs or other convenient accounts or options. This may encourage members/patients to pay back providers and reduce underpayment to providers.

FIG. 1 illustrates an embodiment of a healthcare payment management system 100 for improving and facilitating the payment process from members/patients to providers. The healthcare payment management system 100 may comprise a payment consolidation server 110, one or more provider interfaces 120, one or more payer interfaces 130, and a member interface 140, which may be coupled to each other via one or more networks 150. The healthcare payment management system 100 may comprise any number of such components, which may be arranged as shown in FIG. 1.

The payment consolidation server 110 may be any component, device, or apparatus configured to process, store, and exchange payments information that may be due from members to providers for care services. For instance, the payment consolidation server 110 may be a physical sever or a general-purpose computer, e.g., at a data center or a network. The payments information may comprise billing statements from providers, EOBs from payers, and optionally other relevant information for provided care and/or healthcare plans for members. The payment consolidation server 110 may be configured to process and consolidate the EOBs and billing statements (and optionally any other relevant information) that correspond to members to obtain simplified payment information statements that are relatively easier for members to understand and verify. The payment consolidation server 110 may receive the billing statements from providers, the EOBs from payers, consolidate the EOBs and billing statements (as described below), and forward the resulting payment consolidation information to members.

The payment consolidation server 110 may also be coupled to or comprise at least one storage device 160, which may be a local storage or a remote storage, e.g., in the network 150. For example, the storage device 160 may be a hard disk, a temporary memory device, a portable memory device, or other digital data storage technologies. The storage 160 may be configured to store and maintain the EOBs, billing statements, payment consolidation information, and optionally other relevant information for members, providers, and payers in one or more corresponding databases.

The provider interface 120 may be any component, device, or apparatus configured to send billing statements and optionally other provider and corresponding patients information to the payment consolidation server 110. For example, the provider interface 120 may be a general-purpose computer (e.g., a desktop or laptop computer), a server, a network node, or other communications and processing equipment. Alternatively, the provider interface 120 may be a web portal, an application, or a software system that runs on one or more processors (a computing device or system), such as a provider billing software system that runs on at least one computer or server. The provider interface 120 may send the information automatically to the payment consolidation server 110, e.g., when the information is available and ready to be sent, or regularly (e.g., monthly, quarterly). The provider interface 120 may be part of an office system or an information management system that corresponds to the provider.

The payer interface 130 may be any component, device, or apparatus configured to send EOB statements or information and optionally other payer and corresponding members information to the payment consolidation server 110. For example, the payer interface 130 may be a general-purpose computer (e.g., a desktop or laptop computer), a server, a network node, or other communications and processing equipment. Alternatively, the payer interface 130 may be a web portal, an application, or a software system that runs on one or more processors (a computing device or system), such as a payer management software system that runs on at least one computer or server. The payer interface 130 may send the information automatically to the payment consolidation server 110, e.g., when the information is available and ready to be sent, or regularly (e.g., at determined periods or intervals). For instance, the information from the payer may be sent in real-time upon provider claim adjudication (approval or rejection). The payer interface 130 may be part of an office system or an information management system that corresponds to the payer.

The member interface 140 may be any component, device, or apparatus associated and used by a member/patient and configured to receive the payment consolidation information and optionally any relevant member, provider, and/or payer information. The same member interface 140 may be associated with and used by a plurality of members, e.g., family members or employees for the same employer. Each member may have a corresponding account to access (e.g., using login/password information) and receive corresponding payment consolidation information on the member interface 140. For example, the member interface 140 may be a smartphone, a laptop computer, a tablet computer, an electronic book (ebook) reader, a desktop computer, or other mobile or personal devices that may be used by the member for communications via wired/wireless technologies and suitable networks (e.g., the Internet). Alternatively, the member interface 140 may be an application or a software system that runs on one or more processors (a computing device or system), such as a member billing/payment application that runs on a smartphone, a laptop computer, a tablet computer, an ebook reader, a desktop computer, or other mobile or personal devices.

The network 150 may be any network that communicates with and allows communications between the payment consolidation server 110, the provider interface 120, the payer interface 130, the member interface 140, or combinations thereof. The network 150 may comprise one or a plurality of access/transport networks that may be based on one or more network transport technologies and protocols. Examples of the network 150 may include the Internet, Ethernet networks, optical backbone networks, digital subscriber line (DSL) networks, local area networks (LANs), wireless area networks (WANs), other types of telecommunication networks, or combinations thereof.

To obtain the payment consolidation information, the payment consolidation server 110 may receive data from one or more providers (via one or more provider interfaces 120) that comprise one or more billing statements for one or more episodes of care for a member/patient. For the same episode(s) of care for the member/patient, the payment consolidation server 110 may also receive data from one or more payers (via one or more payer interfaces 130) that comprise one or more EOB statements. The EOB statement(s) or other data from the payer(s) may comprise payer input on adjudicated claim, member deductible status, insurance (payer) and/or insurer (member) payment portions, or combinations thereof. The data from the providers and payers may be received electronically, by mail or other paper based delivery method, or both. As part of the consolidation process, the payment consolidation server 110 may also process member information, such as HSA/FSA information, family information, and/or other member related information. The payment consolidation server 110 may obtain such member information from the payer, a local database, a remote database, or combinations thereof.

The payment consolidation server 110 may reconcile the received data from the provider(s) and payer(s) for the member/patient into a single reconciliation statement or relatively few statements. Accordingly, the payment consolidation server 110 may map between the billing and EOB information in a financial statement balance. In one scenario, member data that indicates status of satisfaction of deductibles and claims adjudication from payers may be reconciled with patient data that indicates accounts receivable status from providers to forward a relatively clear and concise statement to the member/patient. As part of the payment consolidation and reconciliation process, the payment consolidation server 110 may also validate that the provider total billed amount matches the total balance on the EOB, the payer has paid the insurance amount specified on the EOB, and the member has paid the insurer amount specified on the EOB.

The resulting reconciliation statement may also provide one or more payment options for the member/patient. For example, the reconciliation statement may offer the member an option for multiple scheduled payments to complete the total balance. The payment options may also include the option of using HSAs/FSAs of members to pay at least a portion of balance. For instance, the reconciliation statement may show an amount used to pay at least a portion to the total balance from the HSA/FSA account and the amount remaining on the HSA/FSA.

In some scenarios, an owner or operator of the healthcare payment management system 100 may provide the provider a prompt pay option to collect the total amount due by a member before the member makes a payment. This may save the provider time, cost, and effort and guarantee the provider the collection of at least a portion of the payment due. The operator of the healthcare payment management system 100 may be any third party business or enterprise that manages the payment reconciliation process associated with members, providers, and payers (via the payment consolidation server 110). The operator may agree with the provider to pay the provider in advance the amount due at some discount (for example a collection fee), and then seek to collect the full or total amount due from the member. If the operator is successful in collecting the total amount due or a substantial portion of the total amount due, then the operator may make some profit from the difference between the amount paid in advance to the provider and the amount collected subsequently from the member.

The reconciliation statement (including payment options) may be sent to the member/patient electronically (e.g., by email, social media website, text messaging), by mail or other paper based delivery method, or both. For example, the electronic reconciliation statement may be sent electronically as Internet Protocol (IP) packets (or using other networking protocols) and may be displayed on a screen of the member interface 140 or a display device. The EOBs/billings statements may also be available for access from the screen of the member interface 140 or the display device. Additionally, one or more Internet links (e.g., uniform resource locator (URL) links) or other network protocol links for selecting one or more corresponding payment options may be sent electronically to the member, e.g., with the reconciliation statement information packets. When activated by the member (e.g., via the member interface 14), the links may allow the members to make payments via payment transaction systems, such as online credit card payment systems. The billing and EOB statements may also be attached and sent with the reconciliation statement (electronically or by paper-based delivery).

Additionally, the reconciliation server 110 may be configured to manage payment from the member to the provider. The payment may be received from the member, e.g., via the member interface 140, electronically, such as an online credit card payment or other suitable transaction, or by mail or other paper based payment transaction. Thus, the reconciliation server 110 may receive a payment notification from a payment transaction system, e.g., for a bank or a credit card company. A payment confirmation may then be forwarded to the provider, e.g., via the provider interface 120, electronically or by mail or other paper based means.

Figure 2:
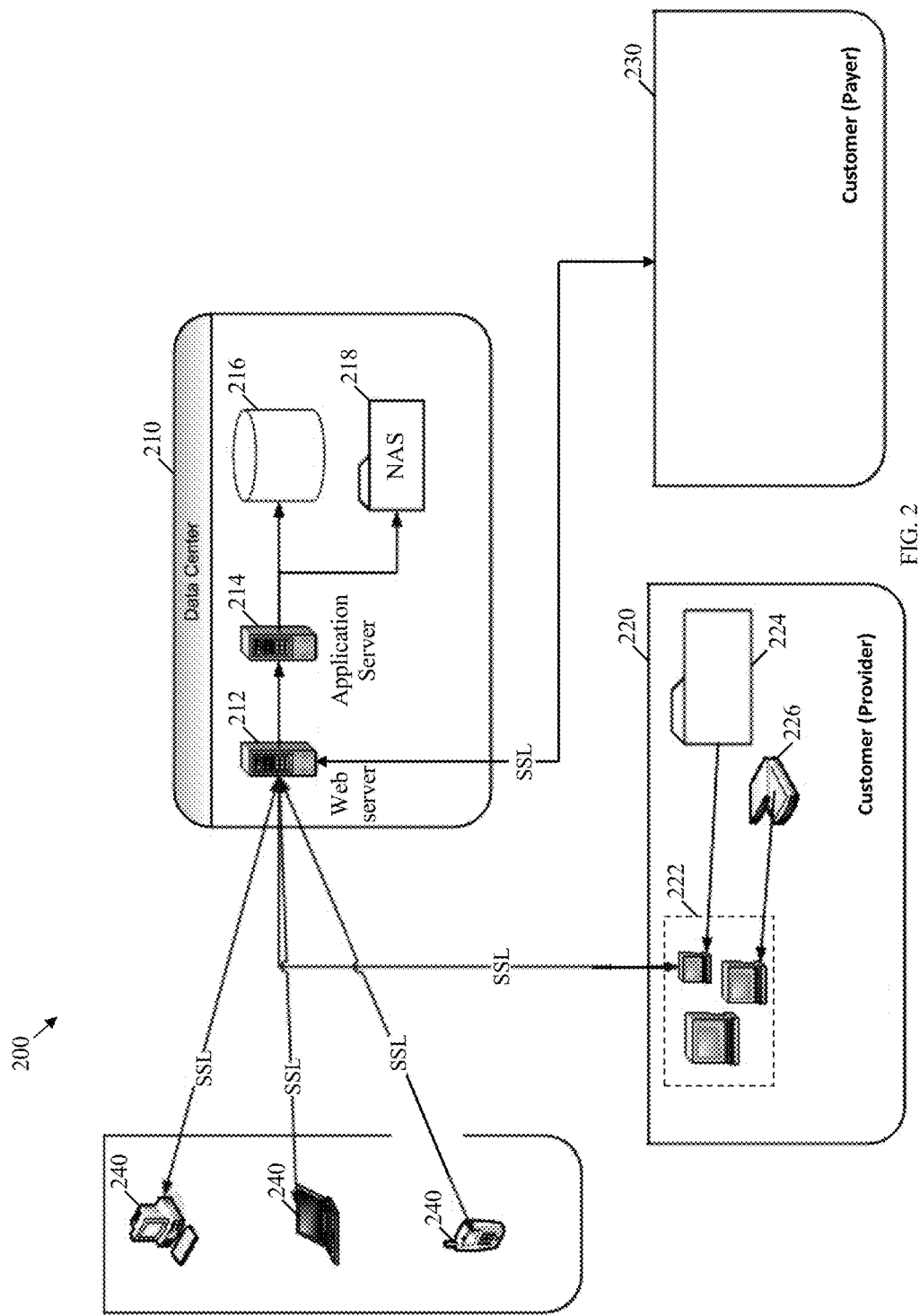
FIG. 2 is a schematic diagram of another embodiment of a healthcare payment management system.

FIG. 2 illustrates an embodiment of another healthcare payment management system 200, which may improve and facilitate payments from members to providers. The healthcare payment management system 200 may comprise a payment consolidation data center 210, a plurality of provider systems 220 and payer systems 230, and one or more interfaces 240. The healthcare payment management system 200 may comprise any number of such components, which may be arranged as shown in FIG. 2.

The payment consolidation data center 210 may be configured to process, store, and exchange data with the interfaces 240, provider systems 220, and payer systems 230. The payment consolidation data center 210 may comprise a web server 212, an application server 214, a local database 216, and optionally a network attached storage (NAS) 218, which may be coupled to each other as shown in FIG. 2. The web server 212 may be configured to receive billing information from the provider systems 220 and EOB information from the payer systems 230, and send reconciled billing/EOB information to the interfaces 240 via network communications (e.g., the Internet). The web server 212 may also receive electronic payment confirmations (e.g., from electronic or online payment transaction systems) for payments made via the interfaces 240 and forward accordingly payment notifications to provider systems 220. The web server 212 may use a secure socket layer (SSL) protocol over the Internet or other networks to exchange the information and data with the other components.

The application server 214 may be configured to process and reconcile billing information received from the provider systems 220 and EOB information from the payer systems 230 to generate reconciliation statements for members, as described above. The application server 214 may also process electronic payment notifications from members to providers, which may indicate charging member accounts (e.g., HSAs/FSAs or bank accounts) and crediting providers accounts, credit card payments from members to providers' accounts, or other online or electronic payment methods from members to providers. Upon receiving the payment notifications, the application server 214 may send corresponding payment, e.g., electronically, to inform the corresponding providers of the payments made by the members.

The web server 212 and application server 214 may be physical severs (hardware) or applications (software) that are implemented on one or more physical servers. The database 216 may be a data structure (software) that maintains the received and/or processed information. The database 216 may be stored locally in a storage device at the payment consolidation data center 210 and/or remotely at the NAS 218. The NAS 218 may comprise one or more storage devices at one or more remote or network locations (e.g., at the Internet or other locations).

The interfaces 240 may be configured substantially similar to the interfaces 140 to receive the reconciliation statements for members from the payment consolidation data center 210. The provider systems 220 may correspond to different providers and may be configured to send billing statements or information (and optionally patient information) to the payment consolidation data center 210. The provider systems 220 may also process payments that may be received electronically from the members. The provider systems 220 may comprise one or more servers/terminals 222 that are configured similar to the provider interfaces 120. The provider systems 220 may also comprise a document/image scanner 224 or similar devices configured to scan documents and statements by users and send the scanned data to the servers/terminals 222. The provider systems 220 may also comprise one or more local storage devices 224 configured to upload documents data stored by users to the servers/terminals 222.

The payer systems 230 may correspond to different payers and may be configured to send EOB statements or information (and optionally member information) to the payment consolidation data center 210. The payer systems 230 may comprise one or more servers/terminals (not shown) that are configured similar the payer interfaces 130. The payer systems 230 may also comprise s document/image scanner (not shown) or similar devices and local storage devices (not shown) similar to the components of the provider systems 220.

The healthcare payment management system 100 and 200 may facilitate and increase the collection of bill payments from members, which may also increase satisfaction of providers and members (insurers), reduce overhead of billing, and provide a revenue stream for providers. A reconciled EOB and billing statement may provide transparency and enhance ease of use for healthcare members/patients. The systems may also provide incentives to members/patients for early payment by accepting first partial payments (or down payments) in exchange. The systems may also have the advantage of time savings for members/patients that select electronic payments through the systems. For example, the members may make payments using links to payment transaction systems (online payment services), which may be provided or forwarded to the members. Providers may benefit from faster collections, higher overall collections, and reduction in collection costs. Both payers and providers may also have reduced print, mail, and postage costs and improved customer satisfaction.

Figure 3:
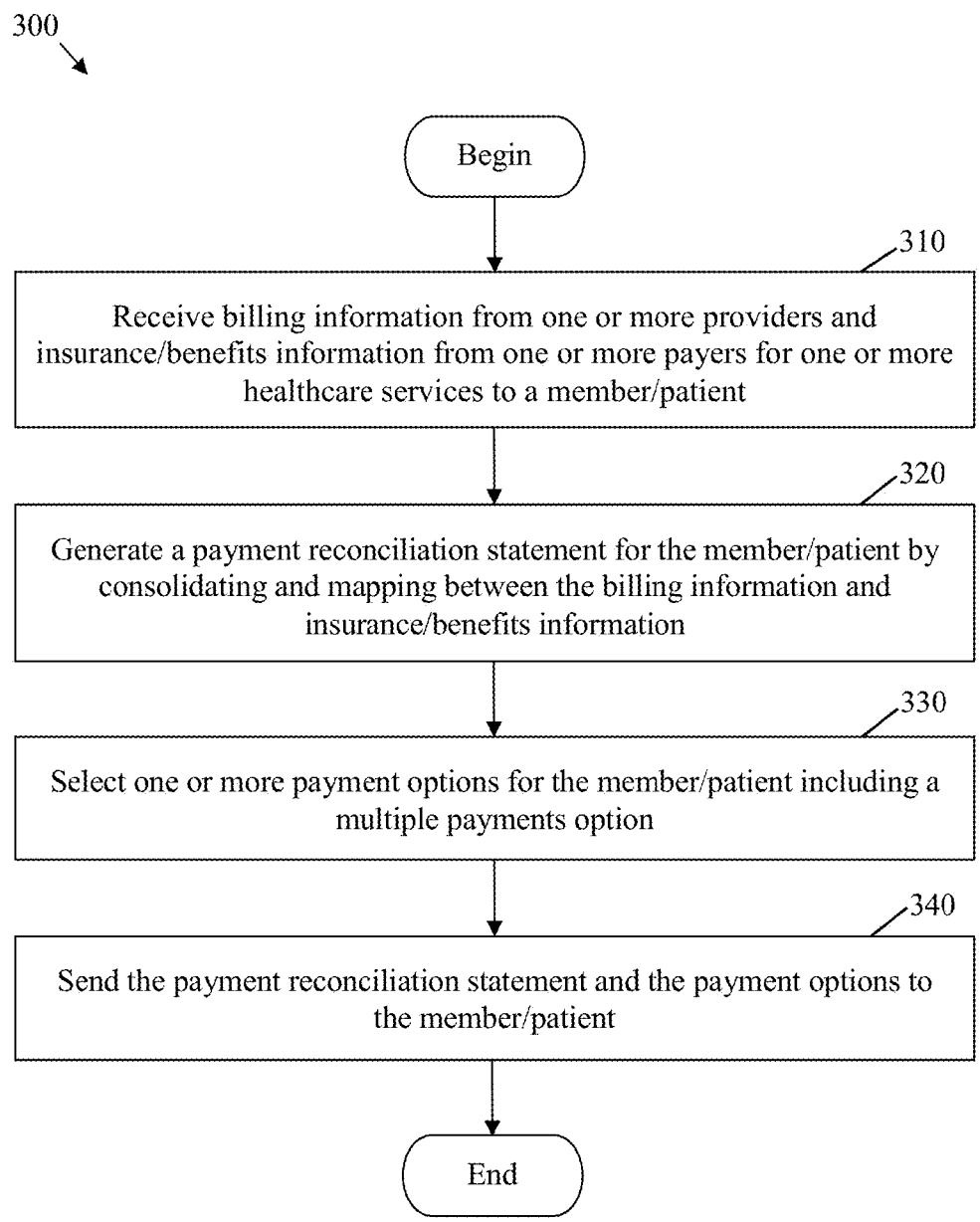
FIG. 3 is a flowchart of an embodiment of a healthcare payment management method.

FIG. 3 illustrates an embodiment of a healthcare payment management method 300, which may be implemented by the healthcare payment management systems 100 and 200. The method 300 may receive billing information from providers, EOB information from payers, and optionally other information as described above, and process the information to provide reconciled statements to members/patients. The reconciled statements may map between billing statements and EOBs to provide a consolidated balance to the member that may be easily examined in view of the billing and EOB information. The method 300 may also provide the members/patients means and options to pay for owed charges for services by providers. The consolidation of billing and EOB information into a reconciled balance and the offering of convenient means to send payments from members may increase collections for providers and benefit all parties, as described above.

The method 300 may begin at block 310, where billing information may be received from one or more providers and insurance/benefits information may be received from one or more payers for one or more healthcare services to a member/patient. For instance, the payment consolidation server 110 may receive billing statements via the provider interface 120 and EOB statements via the payer interface 130. The information may be received electronically, by mail, via email, other communications, or combinations thereof. The healthcare services may correspond to an episode of care that involves a plurality of clinical and treatment visits of the member to different providers. The billing information may comprise a plurality of billing statements that are issued from different providers for the different clinical and treatment visits of the member. The insurance/benefits information may comprise one or more EOB statements form one or more payers for the provided healthcare services. The billing information and/or insurance/benefits information may be forwarded promptly (e.g., after generating the statements for the clinical and treatment visits for the episode of care) or at regular intervals (e.g., weekly, monthly, or quarterly). In some embodiments, the information may be forwarded substantially simultaneously, e.g., when the patient/member is still at the provider facility (during the clinical and treatment visits).

At block 320, a payment reconciliation statement may be generated for the member/patient by consolidating and mapping between the billing information and insurance/benefits information. For instance, the payment consolidation server 110 or the payment consolidation data center 210 may generate a single reconciliation statement that indicates a total balance owed to the member. The total balance may be calculated based on all the received billing and EOB information from one or more providers and payers for the same episode of care to the member. The total balance may include any payments the payer will make or has made on behalf of the member for the episode of care. In the case of multiple billing statements from multiple providers for the same episode of care, a total balance may be calculated for each provider as the difference between the total charge amount from that provider and the covered or paid amount from the payer(s) that provide(s) the coverage benefit. The total balance may be calculated as the difference between the total charges for the provider in the billing statements and the totaled covered or paid amount by payer(s) in the EOB statements.

At block 330, one or more payment options may be selected for the member/patient including a multiple payments option. For instance, the member/patient may be allowed to use pre-established accounts, such as HSA or FSA, to pay the provider(s) for the episode of care. The member/patient may also be offered to pay a percent of the total balance as a down payment if payment is made within a determined time, which may incentivize members to pay and accelerate collections for providers. A plurality of remaining partial payments to cover the balance owed may be scheduled and collected from the member/patient appropriately. When multiple providers are involved in the same episode of care, one or more payment options may be provided for each of the providers.

At block 340, the payment reconciliation statement and the payment options may be sent to the member/patient, e.g., via an interface 140 operated by the member/patient. This reconciliation statement and the payment options may be sent electronically, by mail, via email, other communications, or combinations thereof. The method 300 may then end. The reconciliation statement and the payment options may be may be sent promptly (e.g., after processing and consolidating the billing information and the insurance/benefits information) or at regular intervals (e.g., weekly, monthly, or quarterly). In some embodiments, the reconciliation statement and/or the payment options may be sent substantially simultaneously with the providence of care by the provider, e.g., when the patient/member is still at the provider facility (during the clinical and treatment visits).

Figure 4:
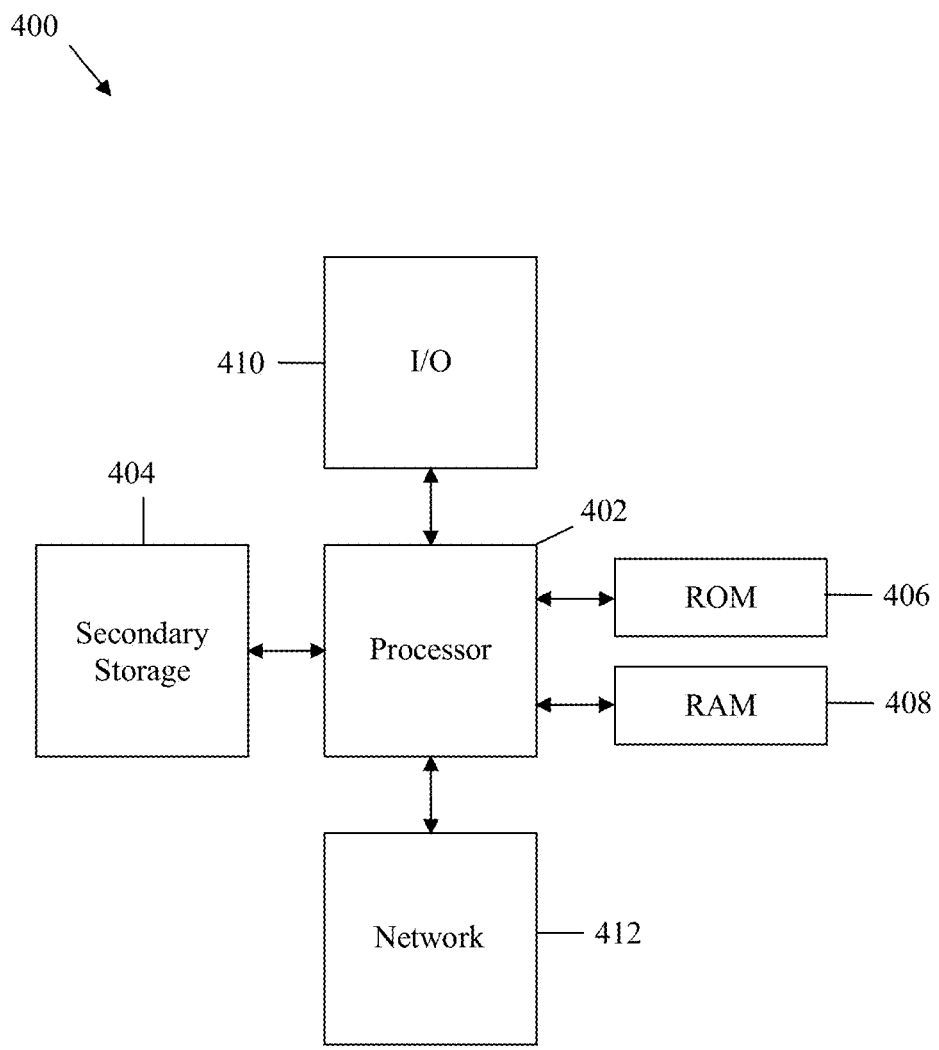
FIG. 4 is a schematic diagram of an embodiment of a general-purpose computer system.

The components described above may be implemented on any general-purpose network component, such as a computer or mobile device with sufficient processing power, memory resources, and network throughput capability to handle the necessary workload placed upon it. FIG. 4 illustrates a typical, general-purpose network component 400 suitable for implementing one or more embodiments of the components disclosed herein. The network component 400 includes a processor 402, e.g., a central processing unit (CPU), which is in communication with memory devices including secondary storage 404, read only memory (ROM) 406, random access memory (RAM) 408, input/output (I/O) devices 410, and network connectivity devices 412. The processor 402 may be implemented as one or more central processing unit (CPU) chips, or may be part of one or more application specific integrated circuits (ASICs) and/or digital signal processors (DSPs). The processor 402 may be configured to implement or support the healthcare payment consolidation schemes of the healthcare payment management systems 100 and 200 and the healthcare payment management method 300.

The secondary storage 404 is typically comprised of one or more disk drives or tape drives and is used for non-volatile storage of data and as an over-flow data storage device if RAM 408 is not large enough to hold all working data. Secondary storage 404 may be used to store programs that are loaded into RAM 408 when such programs are selected for execution. The ROM 406 is used to store instructions and perhaps data that are read during program execution. ROM 406 is a non-volatile memory device that typically has a small memory capacity relative to the larger memory capacity of secondary storage 404. The RAM 408 is used to store volatile data and perhaps to store instructions. Access to both ROM 406 and RAM 408 is typically faster than to secondary storage 404.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 7 percent, . . . , 70 percent, 71 percent, 72 percent, . . . , 97 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A payment consolidation server for completing an online transaction, the payment consolidation server comprising:
a communications interface configured to:
communicate electronically with a plurality of provider servers and a payer server;
receive billing information from the plurality of provider servers for a single episode of care for a member; and
receive benefit information from the payer server for the single episode of care;
a computer processor coupled to the communication interface and configured to:
consolidate the billing information and the benefit information into a payment reconciliation statement by mapping the billing information and the benefit information; and
combine payment links for a plurality of payment options with the billing information and the benefit information to form a website that comprises information from a provider web portal of the plurality of provider servers and from a payer web portal of the payer server, the website presenting the payment reconciliation statement with the plurality of payment options on a user interface to increase payments to a plurality of providers from the member for the single episode of care based at least in part by allowing the member to make payments to the plurality of providers using multiple ones of the plurality of payment options, the payment reconciliation statement indicating for the single episode of care a total payment balance owed by the member to each of the plurality of providers, the total payment balance owed to each of the plurality of providers being calculated as a difference between total charges for the provider in the billing information and a total covered by a payer in the benefit information, the payment reconciliation statement comprising the plurality of payment options for each of the plurality of providers, the plurality of payment options including a healthcare account option and a partial payment option, the payment reconciliation statement being provided to the member on the user interface, the payment reconciliation statement listing each of the plurality of providers for the single episode of care and the total payment balance owed to each of the plurality of providers, the payment reconciliation statement presenting the plurality of payment options for each of the plurality of providers on the user interface, the plurality of payment options including the healthcare account option, the partial payment option, and a pay-in-full option, the payment options including an option to pay by credit card and an option to pay by a check from a banking account, and the partial payment option allowing the member to use a pre-established healthcare account to pay a percentage of the total payment balance owed to each of the plurality of providers as a down payment and pay a remainder of the total payment balance owed to each of the plurality of providers over a scheduled amount of time;
the communications interface being further configured to:
send the payment reconciliation statement electronically to the member; and
send an electronic payment confirmation to the plurality of providers based on receiving an indication of a payment made from the member to a third-party payment transaction system, the electronic payment confirmation indicating a charging of an account associated with the member and a crediting of an account associated with the plurality of providers; and
the computer processor being further configured to complete the online transaction by performing a validation process with an Explanation of Benefits (EOB) statement, the validation process comprising the payment consolidation server validating that the total payment balance owed to each of the plurality of providers matches a total payment balance on the EOB statement, that the member has paid an insurance amount specified on the EOB statement, and that the member has paid an insurer amount specified on the EOB statement.

2. The payment consolidation server of claim 1, wherein the healthcare account option comprises providing the member an option to pay with a health savings account (HSA) and an option to pay with a flexible spending account (FSA).

3. The payment consolidation server of claim 1, wherein the payment consolidation server is configured to receive the billing information from the plurality of provider servers and the benefit information from the payer server automatically in real-time as the billing information and the benefit information become available.

4. The payment consolidation server of claim 1, wherein the payment consolidation server is configured to receive the billing information from the plurality of provider servers and the benefit information from the payer server at regularly scheduled time intervals.

5. The payment consolidation server of claim 1, wherein the billing information, the benefit information, and the payment reconciliation statement are exchanged electronically.

6. The payment consolidation server of claim 1, wherein the healthcare payment management system comprises multiple members, and each of the multiple members having a login and a password to access the healthcare payment management system.

7. The payment consolidation server of claim 1, further comprising a database coupled to the computer processor, the database configured to store the billing information from the plurality of provider servers and the benefit information from the payer server, and the computer processor being further configured to retrieve the billing information from the plurality of provider servers and the benefit information from the payer server to complete the online transaction.

8. An apparatus for completing an online transaction in a healthcare payment management system, the apparatus comprising:
a computer processor; and
a communications interface coupled to the computer processor,
the computer processor being configured to:
receive through the communications interface multiple billing statements from multiple provider servers for a single episode of care for a member;
receive through the communications interface multiple explanation of benefit (EOB) statements from one or more payer servers for the single episode of care;
consolidate the multiple billing statements and the multiple EOB statements by mapping billing information and benefit information using the computer processor to provide a total payment balance owed by the member to each one of a plurality providers for the single episode of care;

combine payment links for a plurality of payment options with the multiple billing statements and the multiple EOB statements to form a website that comprises information from a provider web portal of the multiple provider servers and from a payer web portal of the one or more payer servers, the website presenting a payment reconciliation statement with the plurality of payment options on a user interface to increase payments to a plurality of providers from the member for the single episode of care based at least in part by allowing the member to make payments to the plurality of providers using multiple ones of the plurality of payment options, the total payment balance owed by the member to each one of the plurality of providers being calculated as a difference between total charges for the provider in the multiple billing statements and a total covered by a payer in the multiple EOB statements, the payment reconciliation statement comprising the plurality of payment options for each of the plurality of providers, the plurality of payment options including a healthcare account option and a partial payment option, the payment reconciliation statement being provided to the member on the user interface, the payment reconciliation statement listing each of the plurality of providers for the single episode of care and the total payment balance owed to each of the plurality of providers, the payment reconciliation statement presenting the plurality of payment options for each of the plurality of providers on the user interface, the plurality of payment options including the healthcare account option, the partial payment option, and a pay-in-full option, the payment options including an option to pay by credit card and an option to pay by a check from a banking account, the partial payment option allowing the member to use a pre-established healthcare account to pay a percentage of the total payment balance owed to each of the plurality of providers as a down payment and pay a remainder of the total payment balance owed to each of the plurality of providers over a scheduled amount of time;

send an electronic payment confirmation to the plurality of providers based on receiving an indication of a payment made from the member to a third-party payment transaction system, the electronic payment confirmation indicating a charging of an account associated with the member and a crediting of an account associated with the plurality of providers; and complete the online transaction by performing a validation process with the multiple EOB statements, the validation process comprising validating that the total payment balance owed to each of the plurality of providers matches a total payment balance on the multiple EOB statements, that the member has paid an insurance amount specified on the multiple EOB statements, and that the member has paid an insurer amount specified on the multiple EOB statements.

9. The apparatus of claim 8, wherein the healthcare account option comprises providing the member with an option to pay with a health savings account (HSA) and an option to pay with a flexible spending account (FSA).

10. The apparatus of claim 8, wherein the plurality of payment options include an option that is provided as an Internet link that enables the member to make a payment for the total payment balance, a first partial payment, and/or subsequent payments electronically.

11. The apparatus of claim 8, wherein the apparatus comprises multiple members, and each of the multiple members having a login and a password to access a healthcare payment management system.

12. The apparatus of claim 8, further comprising a database coupled to the computer processor, the database configured to store the billing information from the plurality of provider servers and the benefit information from the payer server, and the computer processor being further configured to retrieve the billing information from the plurality of provider servers and the benefit information from the payer server to complete the online transaction.

13. A payment consolidation server for completing an online transaction, the payment consolidation server comprising:

a computer processor; and a communications interface coupled to the computer processor, the computer processor being configured to:

receive through the communications interface billing information from a plurality of providers for a single episode of care for a member;

receive through the communications interface benefit information from a payer for the single episode of care;

consolidate the billing information and the benefit information into a payment reconciliation statement by mapping the billing information and the benefit information;

combine payment links for a plurality of payment options with the billing information and the benefit information to form a website that comprises information from a provider web portal of the plurality of providers and from a payer web portal of the payer, the website presenting the payment reconciliation statement with the plurality of payment options on a user interface to increase payments to the plurality of providers from the member for the single episode of care based at least in part by allowing the member to make payments to the plurality of providers using multiple ones of the plurality payment options, the payment reconciliation statement indicating for the single episode of care a total payment balance owed by the member to each of the plurality of providers, the total payment balance owed to each of the plurality of providers being calculated as a difference between total charges for the provider in the billing information and a total covered by the payer in the benefit information, the payment reconciliation statement comprising the plurality of payment options for each of the plurality of providers, the plurality of payment options including a healthcare account option and a partial payment option, the payment reconciliation statement being provided to the member on the user interface, the payment reconciliation statement listing each of the plurality of providers for the single episode of care and the total payment balance owed to each of the plurality of providers, the payment reconciliation statement presenting the plurality of payment options for each of the plurality of providers on the user interface, the plurality of payment options including the healthcare account option, the partial payment option, and a pay-in-full option, the payment options including an option to pay by credit card and an option to pay by a check from a banking account, and the partial payment option allowing the member to use a pre-established healthcare account to pay a percentage of the total payment balance owed to each of the plurality of providers as a down payment and pay a remainder of the total payment balance owed to each of the plurality of providers over a scheduled amount of time;

send the payment reconciliation statement electronically to the member;

send an electronic payment confirmation to the plurality of providers based on receiving an indication of a payment made from the member to a third-party payment transaction system, the electronic payment confirmation indicating a charging of an account associated with the member and a crediting of an account associated with the plurality of providers; and complete the online transaction by performing a validation process with an Explanation of Benefits (EOB) statement, the validation process comprising the payment consolidation server validating that the total payment balance owed to each of the plurality of providers matches a total payment balance on the EOB statement, that the member has paid an insurance amount specified on the EOB statement, and that the member has paid an insurer amount specified on the EOB statement.

14. The payment consolidation server of claim 13, wherein the account associated with the member comprises a medical account associated with the member.

15. The payment consolidation server of claim 13, wherein the single episode of care involves a plurality of clinical and treatment visits of the member to the plurality of providers, and the billing information being issued from the plurality of providers for the different clinical and treatment visits of the member.

16. The payment consolidation server of claim 13, further comprising a database coupled to the computer processor, the database configured to store the billing information from the plurality of provider servers and the benefit information from the payer server, and the computer processor being further configured to retrieve the billing information from the plurality of provider servers and the benefit information from the payer server to complete the online transaction.

* * * * *